(12) United States Patent
Bergbreiter et al.

(10) Patent No.: US 12,208,377 B2
(45) Date of Patent: Jan. 28, 2025

(54) SOLVENTS FOR ORGANOMETALLIC REAGENTS

(71) Applicant: The Texas A&M University System, College Station, TX (US)

(72) Inventors: David E. Bergbreiter, College Station, TX (US); Thomas J. Malinski, Bryan, TX (US)

(73) Assignee: The Texas A&M University System, College Station, TX (US)

( * ) Notice: Subject to any disclaimer, the term of this patent is extended or adjusted under 35 U.S.C. 154(b) by 23 days.

(21) Appl. No.: 17/263,536

(22) PCT Filed: Jul. 30, 2019

(86) PCT No.: PCT/US2019/044193
§ 371 (c)(1),
(2) Date: Jan. 26, 2021

(87) PCT Pub. No.: WO2020/028399
PCT Pub. Date: Feb. 6, 2020

(65) Prior Publication Data
US 2021/0178375 A1    Jun. 17, 2021

Related U.S. Application Data

(60) Provisional application No. 62/711,892, filed on Jul. 30, 2018.

(51) Int. Cl.
| | |
|---|---|
| B01J 37/04 | (2006.01) |
| B01J 31/06 | (2006.01) |
| B01J 31/12 | (2006.01) |
| B01J 35/27 | (2024.01) |
| C07C 33/20 | (2006.01) |
| C07C 49/76 | (2006.01) |
| C07C 233/65 | (2006.01) |

(52) U.S. Cl.
CPC ............. *B01J 31/122* (2013.01); *B01J 31/06* (2013.01); *B01J 35/27* (2024.01); *B01J 37/04* (2013.01); *C07C 33/20* (2013.01); *C07C 49/76* (2013.01); *C07C 233/65* (2013.01); *B01J 2231/12* (2013.01); *B01J 2231/342* (2013.01); *B01J 2231/44* (2013.01); *B01J 2531/11* (2013.01)

(58) Field of Classification Search
CPC .................................. B01J 31/06; B01J 37/04
USPC ............................................................ 585/17
See application file for complete search history.

(56) References Cited

U.S. PATENT DOCUMENTS 6,248,702 B1 *   6/2001   Coolbaugh ............. C10L 10/04
                                                                525/298

OTHER PUBLICATIONS

Liang et al. Angew. Chem. Int. Ed. Year 2014, 53, 8084-8087.*
Supporting Information: Harrell al. J. Polymer Science, Year 2014, 52, 545-551.*
Harrell dissertation: Studies of Alternative Solvent Systems to Recycle Phase Selectively Soluble Catalyst, Dec. 2017, pp. 1-156.*
Harrell, Mary L. et al.; "Alternatives for Conventional Alkane Solvents"; Journal of the American Chemical Society; vol. 138; Oct. 18, 2016; pp. 14650-14657.
Priyadarshani, Nilusha et al.; "Polyolefin Soluble Polyisobutylene Oligomer-Bound Metallophthalocyanine and Azo Dye Additives"; Journal of Polymer Science, Part A: Polymer Chemistry; vol. 52; Nov. 30, 2013; pp. 545-551.
Samunual, Peerada et al.; "$S_N2$ Reactions in Hydrocarbon Solvents Using Ammonium-Terminated Polyisobutylene Oligomers as Phase-Solubilizing Agents and Catalysts"; The Journal of Organic Chemistry; vol. 83; Jul. 27, 2018; pp. 11101-11107.
Malinski, Thomas J. et al.; "Safer solvents for reactive organometallic reagents"; Tetrahedron Letters; vol. 59; Sep. 17, 2018; pp. 3926-3929.

* cited by examiner

*Primary Examiner* — Ana Z Muresan
(74) *Attorney, Agent, or Firm* — Winstead PC

(57) ABSTRACT

A solution consisting of: a poly(a-olefin) (PAO) selected from the group consisting of $PAO_{283}$, $PAO_{432}$, and $PAO_{687}$; and
a reactive organometallic reagent selected from the group consisting of n-butyllithium, sec-butyllithium, tert-butyllithium, n-butyllithium in hexane, sec-butyllithium in cyclohexane, and tert-butyllithium in pentane.

4 Claims, 2 Drawing Sheets

SOLVENTS FOR ORGANOMETALLIC REAGENTS

CROSS-REFERENCE TO RELATED APPLICATIONS

This patent application claims priority from, and incorporates by reference the entire disclosure of, U.S. Provisional Patent Application No. 62/711,892 filed on Jul. 30, 2018.

TECHNICAL FIELD

The present disclosure relates generally to solvents and more particularly, but not by way of limitation, to compositions and methods for solvents for organometallic reagents.

BACKGROUND

This section provides background information to facilitate a better understanding of the various aspects of the disclosure. It should be understood that the statements in this section of this document are to be read in this light, and not as admissions of prior art.

The present disclosure describes the use of poly(α-olefin)s (PAOs) as safer alternatives to cyclohexane, hexanes, and heptane as solvents for highly reactive organometallic compounds like alkyllithium reagents. While PAOs like any alkane are flammable, PAOs do not readily catch on fire because they contain 20 or more carbon atoms, a low volatility, and have a high flash point vis-à-vis alkanes like hexane. Also unlike conventional alkanes, PAOs can be quantitatively separated from polar organic solvents and polar organic products either by simple gravity separation or by extraction after a reaction. Any leaching of the PAO solvent into a polar phase during such a separation can be minimized by the addition of small amounts of water to the polar phase. However, while these PAO solvents have some physical differences from conventional low molecular weight volatile alkanes, they otherwise behave like alkanes. Reactive organometallic reagents as exemplified by alkyllithium reagents in these PAO solvents can be used in their conventional reactions in these PAO solvents.

The development of this invention was funded in part by the Welch Foundation under grant number A-0639.

SUMMARY OF THE INVENTION

This summary is provided to introduce a selection of concepts that are further described below in the Detailed Description. This summary is not intended to identify key or essential features of the claimed subject matter, nor is it to be used as an aid in limiting the scope of the claimed subject matter.

In an embodiment, the present disclosure pertains to a solvent including a hydrocarbon oligomer with at least 20 carbon atoms, where the hydrocarbon oligomer has at least one of a low viscosity, a low vapor pressure, and a high flashpoint. In some embodiments, the solvent can include, without limitation, a poly(α-olefin) decene dimer, a poly(α-olefin) decene trimer, a poly(α-olefin) decene tetramer, a poly(α-olefin) decene pentamer, a poly(α-olefin) dodecene dimer, a poly(α-olefin) dodecene trimer, a poly(α-olefin) dodecene tetramer, a poly(α-olefin)-anchored cosolvent, or combinations thereof. In some embodiments, the poly(α-olefin)-anchored cosolvent is a polyisobutylene-bound cosolvent. In some embodiments, the polyisobutylene-bound cosolvent is a terminally functionalized polyisobutylene having end groups that stabilize or solubilize an organometallic reagent in poly(α-olefin). In some embodiments, the hydrocarbon oligomer has low volatility. In some embodiments, the hydrocarbon oligomer is a saturated hydrocarbon oligomer having 20 carbon atoms. In some embodiments, the hydrocarbon oligomer is a saturated hydrocarbon oligomer having 30 carbon atoms. In some embodiments, the hydrocarbon oligomer is a saturated hydrocarbon oligomer having greater than 20 carbon atoms.

In some embodiments, the hydrocarbon oligomer has similar chemistry as a conventional alkane. In some embodiments, the conventional alkane is a volatile alkane. In some embodiments, the volatile alkane can include, without limitation, pentane, hexane, cyclohexane, heptane, or combinations thereof. In some embodiments, the hydrocarbon oligomer is a poly(α-olefin) (PAO) that can include, without limitation, a poly(α-olefin) decene dimer, a poly(α-olefin) decene trimer, a poly(α-olefin) decene tetramer, a poly(α-olefin) decene pentamer, a poly(α-olefin) dodecene dimer, a poly(α-olefin) dodecene trimer, a poly(α-olefin) dodecene tetramer, a poly(α-olefin)-anchored cosolvent, $PAO_{283}$, $PAO_{432}$, $PAO_{687}$, or combinations thereof.

In some embodiments, the solvent is for an organometallic reagent. In some embodiments, the organometallic reagent can include, without limitation, n-butyllithium, sec-butyllithium, tert-butyllithium, alkylboranes, alkylaluminum reagents, alkylmagnesium reagents, organoboranes, organoboron, organoaluminum reagents, organomagnesium reagents, reagents that are soluble in alkanes, reagents that are soluble in a poly(α-olefin), reagents that are soluble in a poly(α-olefin) comprising a poly(α-olefin)-anchored cosolvent, or combinations thereof.

In another embodiment, the present disclosure pertains to a solution including a poly(α-olefin) and a reactive organometallic reagent. In some embodiments, the poly(α-olefin) (PAO) can include, without limitation, a poly(α-olefin) decene dimer, a poly(α-olefin) decene trimer, a poly(α-olefin) decene tetramer, a poly(α-olefin) decene pentamer, a poly(α-olefin) dodecene dimer, a poly(α-olefin) dodecene trimer, a poly(α-olefin) dodecene tetramer, $PAO_{283}$, $PAO_{432}$, $PAO_{687}$, PAO-anchored cosolvent, or combinations thereof. In some embodiments, the PAO-anchored cosolvent is a polyisobutylene-bound (PIB-bound) cosolvent. In some embodiments, the PIB-bound cosolvent is a terminally functionalized PIB having end groups that stabilize or solubilize the organometallic reagent in poly(α-olefin). In some embodiments, the reactive organometallic reagent can include, without limitation, n-butyllithium, sec-butyllithium, tert-butyllithium, alkylboranes, alkylaluminum reagents, alkylmagnesium reagents, organoboranes, organoboron, organoaluminum reagents, organomagnesium reagents, reagents that are soluble in alkanes, reagents that are soluble in a poly(α-olefin), reagents that are soluble in a poly(α-olefin) comprising a poly(α-olefin)-anchored cosolvent, or combinations thereof.

In a further embodiment, the present disclosure pertains to a solution including an oligomeric hydrocarbon and a reactive organometallic reagent. In some embodiments, the oligomeric hydrocarbon can include, without limitation, a poly(α-olefin) (PAO) decene dimer, a poly(α-olefin) decene trimer, a poly(α-olefin) decene tetramer, a poly(α-olefin) decene pentamer, a poly(α-olefin) dodecene dimer, a poly(α-olefin) dodecene trimer, a poly(α-olefin) dodecene tetramer, $PAO_{283}$, $PAO_{432}$, $PAO_{687}$, a PAO-anchored cosolvent, or combinations thereof. In some embodiments, the PAO-anchored cosolvent is a polyisobutylene-bound (PIB-bound) cosolvent. In some embodiments, the PIB-bound cosolvent is a terminally functionalized PIB having end groups that stabilize or solubilize the organometallic reagent in poly($\alpha$-olefin). In some embodiments, the reactive organometallic reagent can include, without limitation, n-butyl-lithium, sec-butyllithium, tert-butyllithium, alkylboranes, alkylaluminum reagents, alkylmagnesium reagents, organoboranes, organoboron, organoaluminum reagents, organomagnesium reagents, reagents that are soluble in alkanes, reagents that are soluble in a poly($\alpha$-olefin), reagents that are soluble in a poly($\alpha$-olefin) comprising a poly($\alpha$-olefin)-anchored cosolvent, or combinations thereof.

In an additional embodiment, the present disclosure pertains to a method for creating a solution, where the method includes adding a reactive organometallic reagent to an oligomeric hydrocarbon. In some embodiments, the oligomeric hydrocarbon is a poly($\alpha$-olefin) (PAO) that can include, without limitation, a poly($\alpha$-olefin) decene dimer, a poly($\alpha$-olefin) decene trimer, a poly($\alpha$-olefin) decene tetramer, a poly($\alpha$-olefin) decene pentamer, a poly($\alpha$-olefin) dodecene dimer, a poly($\alpha$-olefin) dodecene trimer, a poly($\alpha$-olefin) dodecene tetramer, $PAO_{283}$, $PAO_{432}$, $PAO_{687}$, a PAO-anchored cosolvent, or combinations thereof. In some embodiments, the PAO-anchored cosolvent is a polyisobutylene-bound (PIB-bound) cosolvent. In some embodiments, the PIB-bound cosolvent is a terminally functionalized PIB having end groups that stabilize or solubilize the organometallic reagent in poly($\alpha$-olefin). In some embodiments, the reactive organometallic reagent is selected from the group consisting of n-butyllithium, sec-butyllithium, tert-butyllithium, alkylboranes, alkylaluminum reagents, alkylmagnesium reagents, organoboranes, organoboron, organoaluminum reagents, organomagnesium reagents, reagents that are soluble in alkanes, reagents that are soluble in a poly($\alpha$-olefin), reagents that are soluble in a poly($\alpha$-olefin) comprising a poly($\alpha$-olefin)-anchored cosolvent, or combinations thereof.

BRIEF DESCRIPTION OF THE DRAWINGS

A more complete understanding of the subject matter of the present disclosure may be obtained by reference to the following Detailed Description when taken in conjunction with the accompanying Drawings wherein.

DETAILED DESCRIPTION

Figure 1:
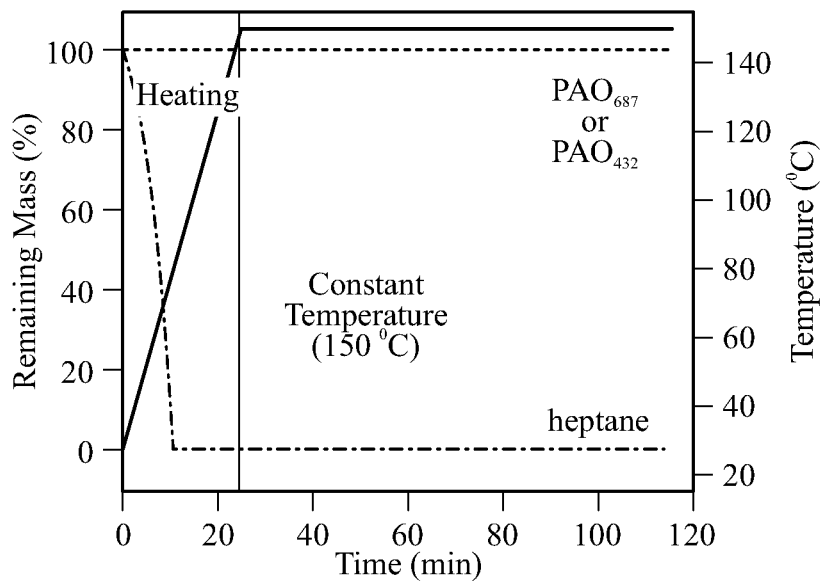
FIG. 1 illustrates TGA of heptane (dashed-dot line) and $PAO_{432}$ and $PAO_{687}$ (dashed line).

It is to be understood that the following disclosure provides many different embodiments, or examples, for implementing different features of various embodiments. Specific examples of components and arrangements are described below to simplify the disclosure. These are, of course, merely examples and are not intended to be limiting. The section headings used herein are for organizational purposes and are not to be construed as limiting the subject matter described.

Reactive organometallic reagents have various uses in organic chemistry. Alkyllithium reagents, for example, were the initial examples of initiators for living polymerizations and are still used in that application. Alkyllithiums are also used as reagents for metalation of aryl halides, as nucleophiles for 1,2-addition to electrophilic functional groups like aldehydes, ketones and esters, as strong bases for generation of regioselective hindered bases like lithium diisopropylamide (LDA), or as reagents for C—H activation in arenes with that form stabilized anions or have suitable directing groups. However, while alkyllithium reagents like n-butyl-, sec-butyl-, or tert-butyllithium that serve in these roles are commercially available and sold in bulk, these reagents are extremely hazardous. At high concentration, the commercially available solutions in alkanes like pentane or hexane can ignite on contact with air. Even in more modest concentrations, their exothermic reaction with water generates sufficient heat to ignite the volatile alkane solvents used to in these commercial reagents, making their use a serious laboratory hazard.

Similar issues exist for other reactive organometallics like KH, alkali metal dispersions, alkylmagnesium, alkylboron, and alkylaluminum reagents. While there are safe ways to handle these reagents, none of these reagents can ever be considered nonhazardous. However, these reagents' hazards can be mitigated, but not eliminated, by dispersing these reactive metal dispersions as suspensions in inert solvents or by diluting highly pyrophoric reagents like alkylaluminum reagents in an inert alkane solvent. Developing poly($\alpha$-olefin)s (PAOs) as sustainable and greener alternatives to conventional alkane solvents are discussed in the present disclosure, and it has been observed that PAOs' flammability is demonstrably different than conventional alkanes. The present disclosure seeks to describe these studies and show that PAOs can serve as inert solvents for n-butyl-, sec-butyl-, and tert-butyllithium. In that role, they behave like conventional alkane solvents. The only difference between PAOs and a low molecular weight alkane is that the conventional alkane solvent is most commonly removed by distillation at reduced pressure. PAOs have to be separated from polar organic products by extraction or chromatography. While either of these separation strategies can work, the simpler process of using a physical gravity-based separation works well for PAOs since PAOs are refined so that they have a specific molecular weight. Because PAO fractions have 20, 30, or more carbons, they have low solubility in polar organic solvents and essentially no solubility in water.

While the use of PAOs as solvents for reactions like those discussed herein is not known, the general idea that a higher molecular weight alkane medium can serve as a safer and more convenient vehicle for a reactive organometallic species has precedent. For example, using paraffin to prepare dispersions of potassium hydride or Grubbs' catalyst has been previously described. Additionally, using polyethylene oligomers as sometimes solid solvents has been described, and it was noted that as waxy solids that they protected transition metal catalysts from reaction with polar reagents. Subsequently, it was noted that solid paraffin can be used as a protective vehicle for many other catalysts. Alternative solvents for reactions involving alkyllithium reagents too have been explored. However, in that previous work, deep eutectic solvents were not used as solvents for the alkyllithium reagents themselves but rather as an alternative reaction medium for the reaction of the alkane solution of the alkyllithium reagent.

While solid paraffins can be used as vehicles for catalysts, they are unlikely to be useful for alkyllithium reagents since they have to be in the melt form to be used to prepare an alkyllithium dispersion. In the case of paraffins or polyethylene oligomers, this typically involves heating to >70° C., a problem for thermally unstable organometallics like alkyllithium reagents. An alternative that has seen use for dispersions of reactive metals and related species is mineral oil. Mineral oil is generally considered a relatively safe material with a history of use as an over-the-counter laxative, as a skin moisturizer, and as cleaning product. However, mineral oil contains a mixture of hydrocarbons ranging from with 12-40 carbons and can also include some aromatic species. The later species could react with some alkyllithium reagents. The smaller molecular weight hydrocarbons also can contaminate an organic product necessitating column chromatography purification. In contrast, PAOs are fully hydrogenated oligomers derived from dimers, trimers, or oligomers of alkenes like decene, or dodecene, that are fractionated into fractions containing ca. 20 (24), 30 (36), or more carbons. The present disclosure uses dimers and trimers of decene containing ca. 20 or 30 carbons that have values of ca. 283 and 432 Da and modest viscosities. Higher molecular weight PAOs have increased viscosity and likely less useful as solvents. While they will form stable solutions with reactive organometallics like alkyllithium reagents, these higher molecular weight PAOs are more viscous. However, all PAOs and especially those with 30 or more carbons have the property that they minimally contaminate polar organic phases in a biphasic liquid/liquid separation. This latter property differentiates them from other materials like mineral oil. While any hydrocarbon contaminants are easily removed by an extraction with hexanes or by column chromatography, $PAO_{432}$ contamination of a polar organic solvent like acetonitrile is in the 10-100 ppm range, a level of contamination that minimizes the need for an extra purification step and that can be further reduced by adding small amounts of water to the polar phase.

Working Examples

Reference will now be made to more specific embodiments of the present disclosure and data that provides support for such embodiments. However, it should be noted that the disclosure below is for illustrative purposes only and is not intended to limit the scope of the claimed subject matter in any way.

General Information. PAOs were provided by Exxon Mobil. All other reagents and solvents were purchased from commercial sources. Reagents were dried over 4 Å molecular sieves before use. $^1$H NMR spectra were recorded on Inova NMR spectrometers operating at 499.59 MHz. Chemical shifts were reported in ppm with reference to $CDCl_3$ at 7.26 ppm. $^{13}$C NMR spectra were recorded on Inova NMR spectrometers operating at 125.72 MHz. Chemical shifts are reported in ppm with reference to $CDCl_3$ at 77.00 ppm. Thermogravimetric analysis was performed under an argon atmosphere using a TGA Q500 thermogravimetric analyzer heating from room temperature to 100 or 150° C. and holding at this temperature for 2 h. Size exclusion chromatography was performed using two Viscotek LT4000L columns in series and THF as the eluent. Polymer molecular weights were determined using triple detectors (refractive index, right angle light scattering, and viscometry) and polystyrene as a standard. Thermogravimetric analysis was performed using about 40 mg of the sample heated on a TGA Q500 thermogravimetric analyzer from room temperature to either 100 or 150° C. at a rate of 5° C. min$^{-1}$ under argon flow of 20 mL/min$^{-1}$.

Preparing Organolithium Reagents in PAOs. To an oven dried 50 mL glass centrifuge tube equipped with a stir bar, 15 mL of dried, degassed PAO was added under a nitrogen atmosphere. Then, 15 mL of the butyllithium reagent in low molecular weight solvent was added via forced syphon, and the low molecular weight solvent was removed via reduced pressure overnight. Alternatively, the alkane solvent can be first removed from the alkyllithium reagent solution. While this forms a more concentrated pyrophoric form of the alkyllithium reagent, adding the appropriate amount of PAO will form a new solution that is equivalent to that obtained by removing the low molecular weight alkane form the PAO/alkane/alkyllithium reagent mixture.

Determining Concentration of Active Organolithium Reagents. A solution of NaOH (0.1024M) was prepared and standardized via titration with KHP and used to determine the concentration of a standard HCl solution (0.1425). To determine the total base concentration of the organolithium reagents, 0.5 mL of the organolithium solutions were added to 20 mL of water, and then titrated with the standard HCl solution to a phenolphthalein endpoint. To determine the residual base concentration of the organolithium reagents, 0.5 mL of the organolithium solutions were added to 2 mL 1,2-dibromoethane, added to 20 mL of water, and then titrated to a phenolphthalein endpoint. The active butyllithium concentration was the difference of these two values.

Stability of Active Organolithium Reagents Dissolved in PAO in Air. Table 1 and Table 2, below, illustrate concentration of active organolithium reagents in air for tert-butyllithium and n-butyllithium, respectively.

TABLE 1

| Time | Total base (M) | Residual base (M) | Active base (M) |
| --- | --- | --- | --- |
| 0 | 1.90 | 0.30 | 1.60 |
| 1 | 1.60 | 0.27 | 1.33 |
| 10 | 1.62 | 0.28 | 1.34 |
| 30 | 1.62 | 0.28 | 1.34 |
| 60 | 1.63 | 0.28 | 1.34 |

TABLE 2

| Time | Total base (M) | Residual base (M) | Active base (M) |
| --- | --- | --- | --- |
| 0 | 1.46 | 0.25 | 1.21 |
| 1 | 1.09 | 0.16 | 0.91 |
| 10 | 1.05 | 0.16 | 0.90 |
| 30 | 1.05 | 0.16 | 0.89 |
| 60 | 1.04 | 0.17 | 0.87 |

Determining Leaching of PAOs into Polar Solvents. In a vial equipped with a magnetic stir bar, 3 mL of purified $PAO_{432}$ or $PAO_{283}$ were added to 3 mL of the polar solvent and stirred at 90° C. for 10 min for MeOH and DMF, and for 24 h for MeCN. The solution was then cooled to room temperature, and water was added to the aqueous samples. The contents of the vials were then transferred to separatory funnels and allowed to stand for 1 h. The phases were separated, and the polar phase was centrifuged for 15 min at 1500 RPM. A small sample of the polar phase was then collected and analyzed via $^1$H NMR spectroscopy to determine the amount of PAO contamination.

Synthesis of 1-Phenyl-1-Propanol. To a flame dried 50 mL round bottomed flask equipped with a magnetic stir bar, 0.32 mL (3 mmol) of bromobenzene in 15 mL dry THF was added at −78° C. Then, n-butyllithium (1.32 mL, 3.3 mmol, 2.5 M in hexane or PAO$_{432}$) was added dropwise and allowed to react for 30 minutes, at which time propionaldehyde (0.26 mL, 3.6 mmol) in 15 mL dry THF was added dropwise. After 1 h, the reaction was quenched with 20 mL saturated ammonium chloride. The phases were separated, and the aqueous phase was washed once with 15 mL hexane. The combined organic phases were washed once with 15 mL 2 M HCl. The organic phase was then dried over sodium sulfate, filtered, and the solvent was removed under reduced pressure. The residue was then taken up in 10 mL hexane and extracted once with 10 mL MeCN. Solvent from the MeCN phase was then removed via reduced pressure to give the product: 89% yield hexanes, 85% yield PAO.

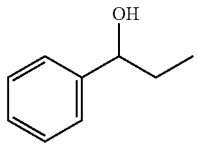

Compound 1

$^1$H NMR (500 MHz, CDCl$_3$) δ=7.25-7.38 (m, 5H), 4.60 (t, J=6.5 Hz, 1H), 1.90 (bs, 1H), 1.79 (m, 2H), 0.92 (t, J=7.5 Hz, 3H); $^{13}$C NMR (125 MHz, CDCl$_3$) δ=144.6, 128.4, 127.5, 125.97, 76.0, 31.9, 10.1

Synthesis of 1-Phenyl-1-Pentanol. To a flame dried 25 mL round bottomed flask equipped with a magnetic stir bar, (0.30 mL, 3 mmol) of benzaldehyde in 3 mL dry THF was added at −78° C. Then, n-butyllithium (1.32 mL, 3.3 mmol, 2.5 M in hexane or PAO$_{432}$) was added dropwise and allowed to react for 2 hours, at which time the reaction was quenched with 10 mL saturated ammonium chloride. The phases were separated, and the aqueous phase was washed once with 10 mL hexane. The combined organic phases were washed once with 10 mL 2 M HCl. The organic phase was then dried over sodium sulfate, filtered, and the solvent was removed under reduced pressure. The residue was then taken up in 10 mL hexane and extracted once with 10 mL MeCN. Solvent from the MeCN phase was then removed via reduced pressure to give the product: 92% yield hexanes, 87% yield PAO.

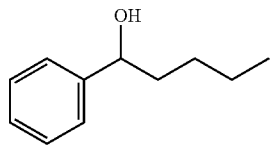

Compound 2

$^1$H NMR (500 MHz, CDCl$_3$) δ=7.25-7.38 (m, 5H), 4.60 (t, J=5 Hz, 1H), 2.02 (bs, 1H), 1.80 (m, 1H), 1.72 (m, 1H), 1.35 (m, 4H), 0.90 (t, J=7 Hz, 3H); $^{13}$C NMR (125 MHz, CDCl$_3$) δ=144.9, 128.4, 127.5, 125.97, 74.7, 38.8, 28.0, 22.6, 14.0

Synthesis of Propiophenone. To a flame dried 50 mL round bottomed flask equipped with a magnetic stir bar, (0.35 mL, 3.3 mmol) of diisopropylamine in 10 mL dry THF was added at −78° C. Then, n-butyllithium (1.32 mL, 3.3 mmol, 2.5 M in hexane or PAO$_{432}$) was added dropwise and allowed to deprotonate for 30 minutes, at which time acetophenone (0.35 mL, 3 mmol) was added and allowed to react for 30 minutes. Then, methyl iodide (0.22 mL, 3.6 mmol) was added in 10 mL dry THF. After 4 h, the reaction was quenched with saturated ammonium chloride. The phases were separated, and the aqueous phase was washed once with 5 mL hexane. The combined organic phases were washed once with 10 mL 2 M HCl. The organic phase was then dried over sodium sulfate, filtered, and the solvent was removed under reduced pressure. The residue was then taken up in 10 mL hexane and extracted once with 10 mL MeCN. Solvent from the MeCN phase was then removed via reduced pressure to give the product: 86% yield hexanes, 89% yield PAO.

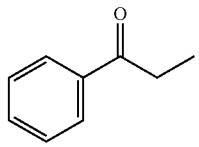

Compound 3

$^1$H NMR (500 MHz, CDCl$_3$) δ=7.95-7.98 (m, 2H), 7.54-7.58 (m, 1H), 7.44-7.49 (m, 2H), 3.02 (t, J=7.2 Hz, 2H), 1.24 (t, J=7.2 Hz, 3H); $^{13}$C NMR (125 MHz, CDCl$_3$) δ=200.8, 136.9, 132.9, 128.5, 127.9, 31.8, 8.2

Synthesis of N,N-Diethylbenzamide. To a 250 mL round bottomed flask equipped with a magnetic stir bar, 6.1 g (50 mmol) benzoic acid and 5.48 g (75 mmol) DMF were dissolved in 100 mL DCM and cooled to 0° C. Then, oxalyl chloride (6.35 g, 50 mmol) was added dropwise, and allowed to react for 2 h, at which time a mixture of diethylamine (5.49 g, 75 mmol) and triethylamine (10.12 g, 100 mmol) was added dropwise, and allowed to react overnight. The resulting suspension was filtered, and the solvent was removed under reduced pressure. The product was purified by silica gel column chromatography (DCM) to yield the product as a yellow oil: 6.1 g, 69% yield.

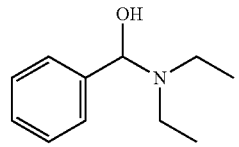

Compound 4

$^1$H NMR (500 MHz, CDCl$_3$) δ=7.35-7.41 (m, 5H), 3.56 (bs, 2H), 3.27 (bs, 2H), 1.26 (bs, 3H), 1.12 (bs, 3H); $^{13}$C NMR (125 MHz, CDCl$_3$) δ=171.3, 137.3, 129.1, 128.4, 126.3, 43.3, 39.2, 14.2, 12.9

Synthesis of N,N-Diethyl-2-Methylbenzamide. To a flame dried 50 mL round bottomed flask equipped with a magnetic stir bar, sec-butyllithium (3.3 mmol, 1.4 M in cyclohexane or PAO$_{432}$) and TMEDA (3.3 mmol) were added to 5 mL dry THF at −78° C. Then, diethylbenzamide (3 mmol) in 10 mL dry THF was added dropwise and allowed to react for 40 minutes, at which time methyl iodide (7.5 mmol) in 5 mL dry THF was added dropwise. After 4 h, the reaction was quenched with 10 mL saturated ammonium chloride. The phases were separated, and the aqueous phase was washed once with 5 mL hexane. The combined organic phases were washed once with 10 mL 2 M HCl. The organic phase was then dried over sodium sulfate, filtered, and the solvent was removed under reduced pressure. The residue was then taken up in 10 mL hexane and extracted once with 10 mL MeCN. Solvent from the MeCN phase was then removed via reduced pressure to give the product as a yellow liquid. The product was further purified by column chromatography (DCM): 62% yield cyclohexane, 66% yield PAO.

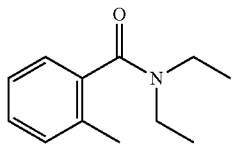

Compound 5

$^1$H NMR (500 MHz, CDCl$_3$) δ=7.14-7.28 (m, 3H), 3.74 (bs, 1H), 3.40 (bs, 1H), 3.11 (q, J=7 Hz, 2H), 2.28 (s, 3H) 1.25 (t, J=7 Hz 3H), 1.02 (t, J=7 Hz, 3H); $^{13}$C NMR (125 MHz, CDCl$_3$) δ=170.8, 137.1, 133.8, 130.3, 128.5, 125.7, 125.4, 42.6, 38.6, 18.8, 14.0, 12.9

Synthesis of Polystyrene. To a flame dried 100 mL round bottomed flask equipped with a magnetic stir bar, 4.0 mL (34.5 mmol) of styrene was added to dried, degassed toluene at room temperature. Then, 0.63 mmol of organolithium reagent in low molecular weight solvent (n-butyllithium in hexane, sec-butyllithium in cyclohexane, tert-butyllithium in pentane) or in PAO$_{432}$ were added in one quick addition. After 1 h, the reaction was quenched with 10 mL methanol, and the solvent was removed via reduced pressure. The crude product was then dissolved in 10 mL DCM and precipitated into 400 mL methanol at 0° C. The product was filtered and dried under vacuum to give the product as a white powder: n-butyllithium in hexane—97% yield, M$_n$ 4100 Da, Đ=2.5; n-butyllithium in PAO$_{432}$—98% yield, M$_n$ 8300, Đ=2.5; tert-butyllithium in pentane—94% yield, M$_n$ 3920 Da, Đ=2.0; tert-butyllithium in PAO$_{432}$—96% yield, M$_n$ 5160, Đ=1.6.

Results and Discussion

While using PAO solvents with M$_n$ values ranging from 687 Da to 2505 Da as solvents has been previously described, these PAOs have 50 to 180 carbons and a higher than desired viscosity. Thus, PAOs that were decene dimers or trimers that have viscosities of 2 and 4 cSt and reported M$_n$ values of 283 and 432 Da, respectively, were used in the present disclosure. These materials' volatility was first examined. In the present disclosure, both PAO$_{432}$ and the previously studied PAO$_{687}$ had minimal mass loss on heating from room temperature to 150° C. (FIG. 1). While PAO$_{283}$ (not shown) did gradually lose significant mass at 150° C., it only had a ca. 3% mass loss over 2 h at 100° C. PAO$_{432}$ and PAO$_{687}$ showed no mass loss even at 150° C. in this same timeframe. Thus the present disclosure focused on solutions of alkyllithium reagents in these two lower viscosity solvents whose viscosity is more amenable for synthetic chemistry.

The PAO solutions of n-butyl-, sec-butyl-, and tert-butyl-lithium were prepared by transferring commercial hexane or cyclohexane solutions of these alkyllithium reagents by forced syphon to a round-bottomed flask containing a known volume of PAO$_{283}$ and/or PAO$_{432}$. The hexane or cyclohexane was then removed from these solutions at reduced pressure until the solution volume approximated that of the PAO$_{283}$ or PAO$_{432}$ solvent. This generally led to a clear solution of the alkyllithium reagent whose titer was measured by a standard titration for alkyllithium and total base. The solutions of n-butyllithium in PAO were typically ca. 2.7 M. The solutions of sec-butyllithium in PAO were typically ca. 1.5 M. The solutions of tert-butyllithium in PAO were typically ca. 1.0 M. While the present disclosure used commercially alkyllithium reagents in low molecular weight alkane solvents, commercially available alkyllithium reagents could be directly synthesized in a PAO solvent, circumventing the need for any low molecular weight alkane solvent.

To demonstrate the lower flammability of the PAO solvents compared to hexane, ca. 20 mL of hexane, 20 mL of PAO$_{432}$, or 20 mL of 1.60 M tert-butyllithium in PAO$_{432}$ was transferred to a petri dish in open air. Notably, the tert-butyllithium solution did not ignite—behavior that was also seen when a similar experiment with 1.21 M n-butyllithium was similarly transferred by forced siphon to a Petri dish in open air. These PAO solutions of alkyllithium reagents were sampled after they were transferred to the petri dish and analyzed for active alkyllithium reagent. Those titratons showed that >80% of the alkyllithium reagent was present even after 30 min. Notably, up to 50% of the active alkyllithium remained after standing in open air overnight.

To further examine flammability, these solutions were exposed to an open flame in the form of a gas torch. As expected, the hexane immediately ignited on exposure to a gas torch. The PAO solutions of the alkyllithium reagents also ignited immediately on exposure to a gas torch, and in all of these experiments, the solutions burned until the solution was completely consumed. However, PAO$_{432}$ that did not contain an alkyllithium reagent was much less flammable. It could be heated with a gas torch for 30 sec without igniting. Further heating did cause the PAO$_{432}$ to smoke and to eventually ignite, though without continued heating by the gas torch the flame self-extinguished within a few seconds. This behavior was seen in repeated versions of the same experiment as well as with any of the higher molecular weight PAO variants. Finally, several 2-mL samples of n-butyl- and tert-butyllithium in PAO$_{432}$ were added to water. None of these experiments led to an ignition event though a similar experiment with tert-butyllithium in pentane did lead to ignition.

To establish the equivalence of alkyllithium reagents in PAO solvents relative to their commercial analogs in low molecular weight alkanes in synthesis, polymerizations, metalation chemistry where the alkyllithium is allowed to react with an aryl bromide to generate an aryllithium reagent, 1,2-additions to aldehydes where the alkyllithium reagent serves as a nucleophile, LDA chemistry where the alkyllithium reagent serves as a base for formation of LDA that is in turn used to form lithium enolates, and C—H activation chemistry where the alkyllithium acts as a strong base to abstract an aryl C—H from a relatively acidic hydrocarbon or from an aryllithium stabilized by a ligating group were examined.

Figure 2:
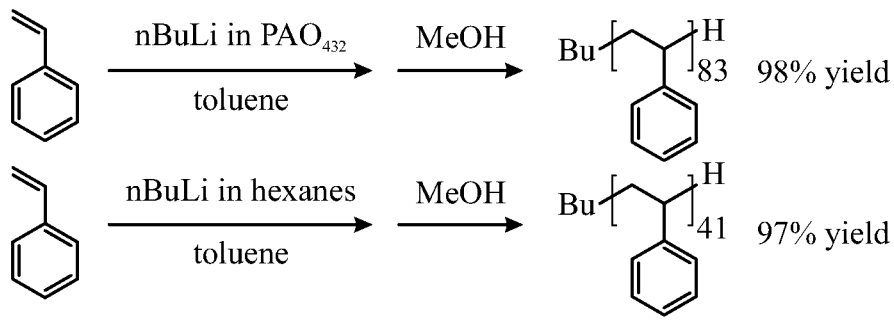
FIG. 2 illustrates styrene polymerizations using either n-BuLi in hexanes or $PAO_{432}$ as an initiator.

The first reaction examined in hexanes versus PAO$_{432}$ was the polymerization of styrene (FIG. 2). In an example of this reaction, a solution of n-butyllithium was added to a toluene solution of styrene at 25° C. that produced a red solution. A MeOH quench led to a clear solution. Solvent removal at reduced pressure afforded a white solid that was purified by precipitation in hexane to afford polystyrene in 97% yield (M$_n$ 4100 Da, Đ=2.5). A reaction with slightly more styrene that used n-butyllithium in PAO$_{432}$ at 25° C. afforded a similar product (M$_n$ 8300, Đ=1.8) in 98% isolated yield. Similar experiments were carried out by adding tert-butyllithium in pentane and PAO$_{432}$ to a toluene solution of styrene. In those cases, polystyrene was isolated in a similar manner with 94 and 96% yield (M$_n$ 3920 Da, Đ=2.0 and M$_n$ 5160, Đ=1.6, respectively.

Figure 3:
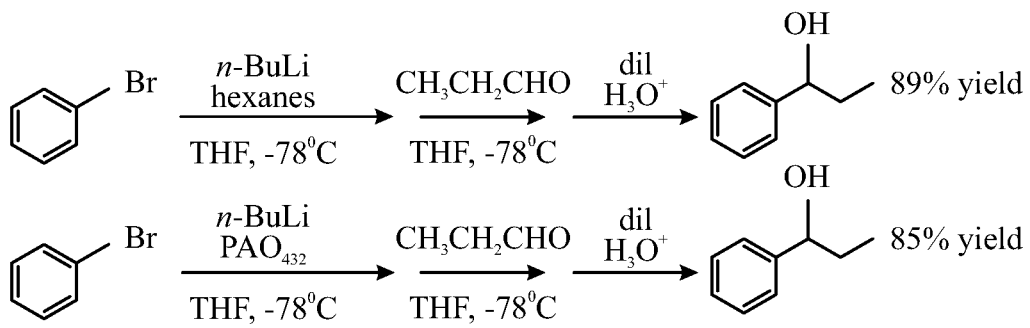
FIG. 3 illustrates transmetalation of bromobenzene to form phenyllithium using either n-BuLi in hexanes/THF or n-BuLi in $PAO_{283}$/THF followed by reaction of the aryllithium reagent with propanal.

The second reaction examined in hexanes versus PAO$_{432}$ was a transmetallation (FIG. 3). In this case, n-butyllithium in hexanes was allowed to react with bromobenzene in THF at −78° C. for 30 min. Propanal was then added, and the reaction was allowed to warm to room temperature. After a dilute aqueous acid quench, the product alcohol was isolated in 89% yield. The same procedure starting with n-butyllithium in PAO$_{432}$ afforded the 1-phenylpropanol product in 85% yield.

Figure 4:
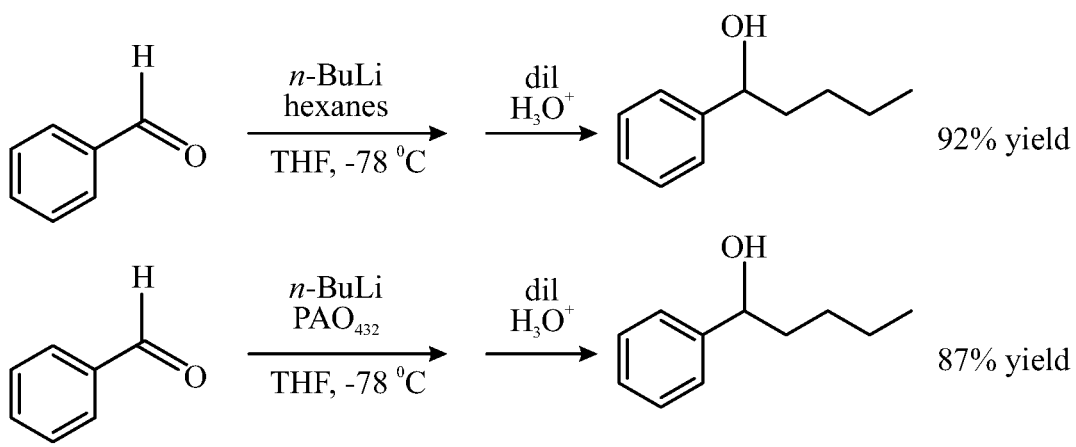
FIG. 4 illustrates 1,2-addition of n-butyllithium in either hexanes/THF or $PAO_{283}$/THF to benzaldehyde.

A third example of the comparability of alkyllithiums in hexanes and PAOs is the 1,2 addition of n-butyllithium to benzaldehyde (FIG. 4). The conventional addition of n-butyllithium to a THF solution of benzaldehyde at −78° C. followed by warming to room temperature and a dilute aqueous acid quench afforded the expected secondary alcohol product in 82% yield. The same procedure starting with n-butyllithium in PAO$_{432}$ afforded the same product in 84% yield.

Figure 5:
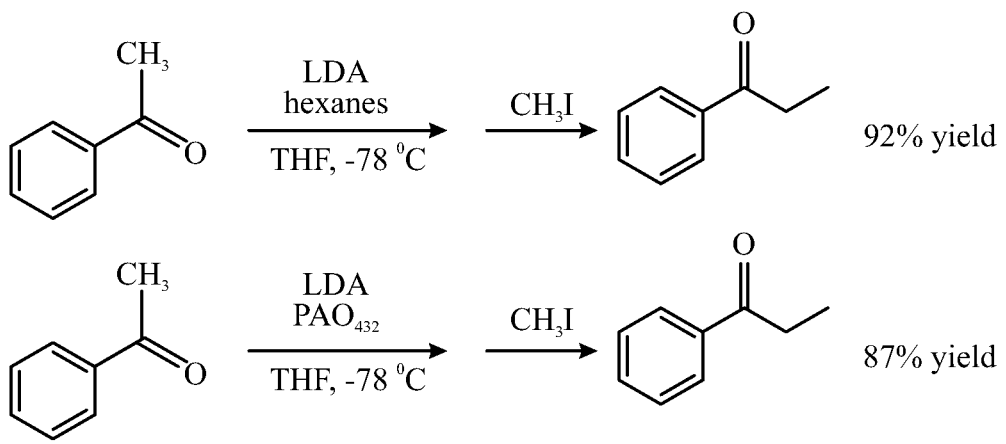
FIG. 5 illustrates methylation of the enolate of acetophenone with methyl iodide using LDA prepared from n-butyllithium in either hexanes/THF or $PAO_{432}$/THF.

Using either n-butyllithium in hexanes or n-butyllithium in PAO$_{283}$ to form LDA to effect an aldol reaction was also equally effective (FIG. 5). In this case, the LDA was prepared at −78° C. from a THF solution of diisopropylamine by addition of the alkyllithium reagent. This LDA solution that contained a modest amount of hexane or PAO$_{283}$ was then allowed to react with acetophenone to form a THF solution of the lithium enolate that was in turn allowed to react with propanal. After warming to room temperature and acidification with dilute acid, the expected aldol product was isolated in 92% and 87% yields, respectively.

Figure 6:
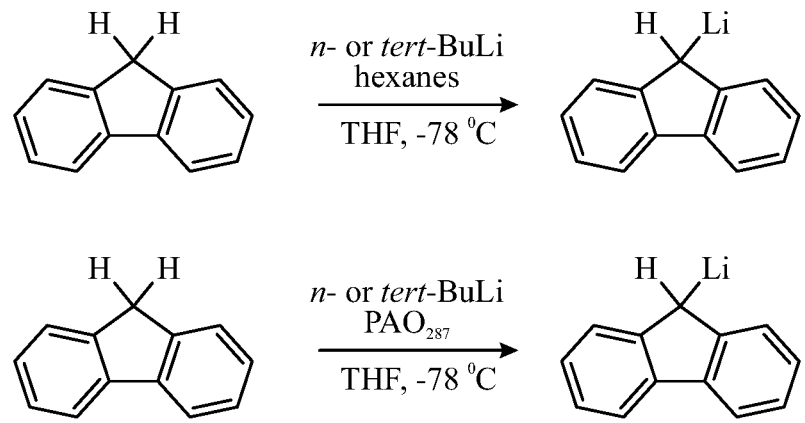
FIG. 6 illustrates lithiation of fluorine by either n- or tert-butyllithium in either hexanes/THF or $PAO_{283}$/THF.

A final example of the equivalence of volatile alkane solutions of alkyllithium reagents with PAO solutions of alkyllithium reagents is their use in metalation of C—H bonds. There are many examples of this chemistry used both in academic and industrial settings. FIG. 6 shows that n- and tert-butyllithium either in hexanes or in PAO$_{283}$ readily deprotonates fluorene. Other metalation chemistry including formation of an aryllithium reagent by a TMEDA facilitated ortho-lithiation of N,N-diethylbenzamide using sec-butyllithium in cyclohexane or PAO$_{432}$ as a solvent was equally effective.

A final aspect of the substitution of PAOs with volatile alkane solvents is that PAOs are easily removed from the products of the reactions in FIGS. 2-6. It was previously described how higher molecular weight and higher viscosity PAOs are separable from solvents like DMF, MeOH, aqueous EtOH and CH$_3$CN. Similar behavior is seen for PAO$_{283}$ and PAO$_{432}$. In experiments that resemble the batch type liquid/liquid extractions typically used to work up a reaction, contamination of PAO$_{283}$ and PAO$_{432}$ was consistently small, see Table 3, below. Moreover, even what contamination of the polar phase that was seen could be reduced ca. 10-fold by adding 20 vol % water to the polar organic phase. Table 3, shown below, illustrates percent leaching of PAO into polar solvents.

TABLE 3

| | DMF | aq DMF | MeOH | aq MeOH | CH$_3$CN |
|---|---|---|---|---|---|
| PAO$_{283}$ | 0.10 | 0.01 | 0.21 | 0.007 | 0.04 |
| PAO$_{432}$ | 0.02 | 0.002 | 0.015 | 0.005 | 0.001 |

Leaching was measured by heating an equivolume mixture of the PAO with MeOH and DMF until the solvent mixture was miscible and then cooling this thermomorphic mixture to room temperature with or without addition of 10 vol % water. The experiments with CH$_3$CN involved 24 h stirring of a biphasic mixture of PAO and CH$_3$CN.

PAO$_{432}$ leaching was further examined in an experiment where PAO$_{432}$ was continuously extracted by CH$_3$CN for an extended period. After 1 d the as received PAO$_{432}$ contaminated the CH$_3$CN phase to the extent of 700 ppm. A second 4 d of continuous extraction of this 'extracted' PAO$_{432}$ led to only 200 ppm contamination of the PAO$_{432}$ in CH$_3$CN. A further 10 d of continuous extraction led to essentially no further extraction of the PAO$_{432}$ into the CH$_3$CN (i.e. <50 ppm).

The results above show that PAO solvents are comparable as solvents to conventional alkanes like pentane, cyclohexane, or hexanes in a variety of alkyllithium chemistry. However, because of their low volatility, n-butyl-, sec-butyl- and tert-butyllithium PAO solutions do not readily inflame. While replacing a low molecular weight alkane by PAO does not make these highly reactive pyrophoric reagents safe, it does mitigate their reactivity. In contrast to conventional alkanes like hexanes or cyclohexane, PAO solvents do not catch on fire even when exposed to flame for minutes. While PAOs are still alkanes and can still burn, alkyllithium reagents in these solvents do not inflame as readily as they would when they are dissolved in low molecular weight alkanes. This suggests that these PAO solvents merit consideration as a vehicle for use with these and other reactive organometallic reagents. Further work to explore other applications of these sustainable, recyclable, and safer solvents in other applications are also envisioned.

Although various embodiments of the present disclosure have been illustrated in the accompanying Drawings and described in the foregoing Detailed Description, it will be understood that the present disclosure is not limited to the embodiments disclosed herein, but is capable of numerous rearrangements, modifications, and substitutions without departing from the spirit of the disclosure as set forth herein.

The term "substantially" is defined as largely but not necessarily wholly what is specified, as understood by a person of ordinary skill in the art. In any disclosed embodiment, the terms "substantially", "approximately", "generally", and "about" may be substituted with "within [a percentage] of" what is specified, where the percentage includes 0.1, 1, 5, and 10 percent.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions, and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a", "an", and other singular terms are intended to include the plural forms thereof unless specifically excluded.

What is claimed is:

1. A solution consisting of:
   a poly(α-olefin) (PAO) selected from the group consisting of PAO$_{283}$, PAO$_{432}$, and PAO$_{687}$; and
   a reactive organometallic reagent selected from the group consisting of n-butyllithium, sec-butyllithium, tert-butyllithium, n-butyllithium in hexane, sec-butyllithium in cyclohexane, and tert-butyllithium in pentane.

2. The solution of claim 1, wherein the reactive organometallic reagent comprises n-butyllithium having a molar concentration of 2.7 M.

3. The solution of claim 1, wherein the reactive organometallic reagent comprises sec-butyllithium having a molar concentration of 1.5 M.

4. The solution of claim 1, wherein the reactive organometallic reagent comprises tert-butyllithium having a molar concentration of 1.0 M.

* * * * *